(12) United States Patent
Coore

(10) Patent No.: US 8,795,646 B2
(45) Date of Patent: Aug. 5, 2014

(54) ORAL PHARMACEUTICAL FORMULATIONS FOR THE TREATMENT OF HUMAN CANITIES

(76) Inventor: Garfield Coore, Scarborough (CA)

(*) Notice: Subject to any disclaimer, the term of this patent is extended or adjusted under 35 U.S.C. 154(b) by 0 days.

(21) Appl. No.: 13/606,837

(22) Filed: Sep. 7, 2012

(65) Prior Publication Data

US 2013/0017260 A1    Jan. 17, 2013

Related U.S. Application Data

(63) Continuation-in-part of application No. PCT/IB2012/051072, filed on Mar. 6, 2012.

(30) Foreign Application Priority Data

Mar. 9, 2011 (CA) .................................... 2733836

(51) Int. Cl.
*A61Q 5/00* (2006.01)

(52) U.S. Cl.
USPC .......................................... 424/70.6; 435/28

(58) Field of Classification Search
USPC .......................................... 424/70.6; 435/28
See application file for complete search history.

(56) References Cited

U.S. PATENT DOCUMENTS 6,005,090 A * 12/1999 Doidge et al. ............... 536/23.5
6,451,341 B1 * 9/2002 Slaga et al. .................... 424/468
2003/0109422 A1 * 6/2003 Mazzone et al. .................... 514/6
2005/0152969 A1 * 7/2005 Chiprich ....................... 424/456
2010/0056425 A1 * 3/2010 New .................................. 514/3
2011/0274680 A1 * 11/2011 Mazed et al. ................. 424/94.4
2011/0287061 A1 * 11/2011 Beggan ......................... 424/400

OTHER PUBLICATIONS de Oliveira, A Nutritious Cocktail for the Treatment of Melanoma: A Case Study, Journal of Orthomolecular Medicine, 1998, vol. 13 No. 3, pp. 176-178.*
Schneider et al., Effects of pterostilbene on melanoma alone and in synergy with inositol hexaphosphate, 2009, vol. 198, pp. 679-684.*
Eiríkur Steingrímsson, Neal G. Copeland and Nancy A. Jenkins. "Melanocyte Stem Cell Maintenance and Hair Graying". Cell, vol. 121, Issue 1, 9-12, 2005.
Spatz, K. R., Overall, R., Klapp, B. F., Arck, P. C., and Peters, E. M. "Increased melanocyte apoptosis under stress mediator Substance P-elucidating pathways involved in stress induced premature graying" Exp. Dermatol. 17, 632, 2008.
Tobin, D. J., Slominski, A., Botchkarev, V., and Paus, R. "The fate of hair follicle melanocytes during the hair growth cycle" J. Investig. Dermatol. Symp. Proc. 4, 323-332, 1999.
Aungst B.J. Intestinal Permeation Enhancers. J Pharm Sci., Apr. 2000; 89(4):429-42.
LeCluyse, E.L., In Vitro for Selection of Develoment Candiates, Permeability Studies to Define Mechanisms of Absorption Enhancement. Adv Drug Deliv Rev. 1997;23:163-183.
Wood, J.M. Senile hair graying: H2O2-mediated oxidative stress affects human hair color by blunting methionine sulfoxide repair. The FASEB Journal. FASEB J. 23:2065-2075 (2009).

* cited by examiner

*Primary Examiner* — Ali Soroush
(74) *Attorney, Agent, or Firm* — Bereskin & Parr LLP/S.E.N.C.R.L., s.r.l.; Michael Fenwick

(57) ABSTRACT

The present application relates generally to oral pharmaceutical formulations for the treatment of human canities.

17 Claims, No Drawings

ORAL PHARMACEUTICAL FORMULATIONS FOR THE TREATMENT OF HUMAN CANITIES

CROSS-REFERENCE TO RELATED APPLICATIONS

This application is a continuation-in-part of PCT International Application PCT/IB2012/051072, filed Mar. 6, 2012, claiming priority to Canadian application no. 2,733,836 filed Mar. 9, 2011.

FIELD

The present application relates generally to oral pharmaceutical formulations for the treatment of canities. In particular, the present application includes an oral pharmaceutical formulation which reduces the amount of hydrogen peroxide in greying hair.

BACKGROUND

Hair greying is an obvious sign of human aging, yet little was known about its cause. Recent papers have attributed hair greying as being due to incomplete melanocyte stem cell maintenance and identify Pax3 and Mitf as key molecules that help regulate the balance between melanocyte stem cell maintenance and differentiation ("Melanocyte Stem Cell Maintenance and Hair Graying", Eirikur Steingrimsson, Neal G. Copeland and Nancy A. Jenkins, Cell, Volume 121, Issue 1, 9-12, 2005). Greying is a natural form of aging, however, greying prematurely can be a source of anxiety and stress. Currently, the main avenue for addressing greying is in the dyeing of hair to cover the grey. Recent studies point to stress as the source of premature greying (Spatz, K. R., Overall, R., Klapp, B. F., Arck, P. C., and Peters, E. M. (2008) "Increased melanocyte apoptosis under stress mediator Substance P-elucidating pathways involved in stress induced premature graying" *Exp. Dermatol.* 17, 632). Still other researchers believe that the biological process of graying is due to the loss of the pigment-forming melanocytes (Tobin, D. J., Slominski, A., Botchkarev, V., and Paus, R. (1999) "The fate of hair follicle melanocytes during the hair growth cycle" *J. Investig. Dermatol. Symp. Proc.* 4, 323-332).

SUMMARY

The present disclosure, in one embodiment, relates to oral pharmaceutical formulations containing at least one hydrogen peroxide reducing enzyme which effectively treats or prevents canities, the loss of hair pigmentation commonly referred to as greying or whitening of hair. Accordingly, in one embodiment, the present disclosure includes an oral pharmaceutical formulation for the treatment of canities in a subject, the formulation comprising a therapeutically effective amount of at least one hydrogen peroxide reducing enzyme.

In one embodiment of the disclosure, the formulation comprises an oral pharmaceutical formulation comprising:
a) at least one hydrogen peroxide reducing enzyme;
b) at least one hydrogen peroxide scavenger; and
c) at least one compound or element which increases gluthathione peroxidase activity in vivo.

Also provided herein, in another embodiment, is an enteric coated liquid capsule oral pharmaceutical formulation for the treatment of canities, comprising:
a) at least one hydrogen peroxide reducing enzyme;
b) at least one hydrogen peroxide scavenger; and
c) at least one compound or element which increases glutathione peroxidase activity in vivo.

In another embodiment, also included is a method of producing said formulations in enteric coated liquid capsules without leakage.

In yet another embodiment, is included a method of treating canities in a subject comprising administering to the subject the oral pharmaceutical formulations described herein.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

DETAILED DESCRIPTION (I) Definitions

The term "oral pharmaceutical formulation" as used herein refers to pharmaceutical formulations that are administered orally and absorbed after ingestion. Oral pharmaceutical formulations include liquids, suspensions, dry powder, pills, tablets, capsules, liquid capsules, solutions, softgels, emulsions, syrups, elixirs, tinctures, and hydrogels.

The term "treatment of canities" as used herein refers to the prevention, treatment, reduction or limiting of the loss of hair pigmentation, or the greying or whitening of hair, or alternatively, increase the amount of pigmented hair.

The term "hydrogen peroxide reducing enzyme" as used herein refers to any enzyme that catalyzes the reduction of $H_2O_2$ to $H_2O$ or any other benign product. Accordingly, the term includes the class of enzymes known as peroxidases (Enzyme Commission Identification No. EC 1.11.1) and the term "peroxidase", as used herein, refers to any individual member of this class. Peroxidases include enzymes of the subclass catalase (Enzyme Commission Identification No. EC 1.11.1.6) and the subclass glutathione peroxidase (Enzyme Commission Identification No. EC 1.11.1.9). The terms "catalase" and "glutathione peroxidase" as used herein refer to any individual enzymes of the aforementioned subclasses.

The term "hydrogen peroxide scavenger" as used herein refers to any compound, element, substance, element or nutrient which reacts, absorbs, chelates or otherwise neutralizes hydrogen peroxide.

The term "compound or element which increases gluthathione peroxidase activity in vivo" as used herein refers to any compound, element, substance, element or nutrient which increases the activity or ability of gluthathione peroxidase to reduce hydrogen peroxide to water.

The term "biomolecule absorption enhancing agent" as used herein refers to agents which increase gastrointestinal absorption and systemic availability (i.e. increased blood/plasma levels) of at least one co-administered biomolecule, nutrient or other compound for which it is desired to increase the absorption and therefore the bioavailability.

The term "enteric coated liquid capsule" as used herein refers to hard- or soft-shelled, banded or un-banded capsules surrounding a liquid fill, which have been treated to resist decomposition in the acid conditions of the stomach.

The term "pharmaceutically-acceptable excipients" as used herein includes any physiologically inert, pharmacologically inactive material known to one skilled in the art, which is compatible with the formulations of the present disclosure.

The term "therapeutically effective amount" as used herein refers to an amount of the pharmaceutical formulation that is used for treating or preventing canities in a subject in need thereof. For those skilled in the art, the therapeutically effective amount, as well as dosage and frequency of administration, may easily be determined according to their knowledge and standard methodology.

The term "liquid sealant coating" as used herein refers to a coating of a liquid capsule which acts as a barrier to control the location in the digestive system where the formulation is absorbed.

The term "acid resistance coating" as used herein refers to a coating of a liquid capsule that slows, resists or stops the degradation of the capsule from undergoing acid erosion in an acidic environment.

(II) Formulations

The present disclosure relates to oral pharmaceutical formulations. In one embodiment the oral pharmaceutical formulations are for the treatment of canities, or to slow, stop, or reverse human hair greying.

In one embodiment, the oral pharmaceutical formulation for the treatment of canities in a subject comprises a therapeutically effective amount of at least one hydrogen peroxide reducing enzyme. In another embodiment, the therapeutically effective amount of the hydrogen peroxide reducing enzyme comprises at least 10,000 IU, optionally at least 10,500 IU, optionally 15,000 IU or optionally about 20,000 IU.

In another embodiment of the disclosure, the formulation comprises an oral pharmaceutical formulation comprising therapeutically effective amounts of:
  a) at least one hydrogen peroxide reducing enzyme;
  b) at least one hydrogen peroxide scavenger; and
  c) at least one compound or element which increases glutathione peroxidase activity in vivo.

In another embodiment, the present disclosure includes an enteric coated liquid capsule oral pharmaceutical formulation for the treatment of canities, comprising a therapeutically effective amount of at least one hydrogen peroxide reducing enzyme. In one embodiment, the therapeutically effective amount of the hydrogen peroxide reducing enzyme comprises at least 10,000 IU, optionally at least 10,500 IU, optionally 15,000 IU or optionally about 20,000 IU.

In another embodiment, the present disclosure includes an enteric coated liquid capsule oral pharmaceutical formulation for the treatment of canities, comprising:
  a) at least one hydrogen peroxide reducing enzyme;
  b) at least one hydrogen peroxide scavenger; and
  c) at least one compound or element which increases glutathione peroxidase activity in viva The formulations of the present disclosure are oral formulations for the treatment of canities, or greying hair. The components of the formulations optionally act synergistically to treat canities by reducing the amount of hydrogen peroxide in the hair shaft. Optionally, the formulations are enteric coated liquid capsules which serve to increase the bioavailability by preventing release of the components in the mouth, stomach or esophagus, but which are released in the small intestines where the components can be quickly absorbed. Further, the liquid capsule also allows for an increase in bioavailability of the components as the components are able to rapidly dissolve in the small intestine. The combination of the components of the oral formulation which act to reduce hydrogen peroxide, as well as the optional enteric coated liquid capsule, serve to increase the ability of the formulation to treat canities.

Hydrogen peroxide is found to accumulate in hair shafts of gray or white hairs. In one embodiment, all of the components of the formulation function to reduce or reverse oxidative damage to follicular melanocytes arising from accumulation of hydrogen peroxide. Further, the components of the formulation provide a synergistic combination for maximizing follicular melanocyte resistance to hydrogen peroxide induced oxidative damage, for preventing oxidant-induced apoptosis of follicular melanocytes, for preventing oxidative inactivation of enzymes involved in melanin synthesis, and/or for preventing hair bleaching.

Hydrogen peroxide reducing enzymes of the formulation actively eliminate reactive hydrogen peroxide species in follicular melanocytes, by neutralizing hydrogen peroxide, thereby increasing cellular ability to resist or reverse accumulations of hydrogen peroxide.

In one embodiment, the hydrogen peroxide reducing enzyme of the formulation is a peroxidase. In another embodiment, the hydrogen peroxide is a catalase or a glutathione peroxidase.

In one embodiment, the hydrogen peroxide reducing enzyme, such as catalase, is present in an amount of at least 5,000 IU, optionally 7,500 IU, optionally 9,000 IU, or 10,000 IU. In one embodiment, the hydrogen peroxide reducing enzyme is present in an amount up to 30,000 IU, optionally 20,000 IU, or about 15,000 IU.

In another embodiment, the hydrogen peroxide reducing enzyme, such as glutathione peroxidase, is present in an amount of at least 0.0001 IU, optionally 1.0 IU, optionally 1,000 IU, 100,000 IU, or about 180,000 IU.

In another embodiment, the formulations also comprise enzymes which catalyze the dismutation of superoxide. In one embodiment, the enzyme which catalyzes the dismutation of superoxide is superoxide dismutase. In one embodiment, the enzyme which catalyzes the dismutation of superoxide is present in an amount of at least 0.0001 IU, optionally 1.0 IU, optionally 1,000 IU, 100,000 IU, or about 180,000 IU.

Hydrogen peroxide scavengers of the formulation serve to react, absorb, or otherwise neutralize hydrogen peroxide, thereby reducing the concentration of hydrogen peroxide.

In one embodiment, the hydrogen peroxide scavenger is an amino acid. In a further embodiment, the scavenger is methionine, cysteine, selenocysteine, or tyrosine. In one embodiment, when the scavenger is methionine, the scavenger serves the additional function of replenishing cellular stores of the essential amino acid methionine. Methionine is depleted by oxidation in gray hair follicles, which are known to be deficient in methionine sulfoxide repair pathways. In one embodiment, the hydrogen peroxide scavenger is L-methionine or DL-methionine.

In another embodiment, the hydrogen peroxide scavenger is present in an amount between In another embodiment, the formulation also includes a compound, element, substance, element or nutrient which increases gluthathione peroxidase activity in vivo which increases the activity or ability of gluthathione peroxidase to reduce hydrogen peroxide to water. For example, the compound or element may increase the expression of the enzyme, or the compound or element may serve as a necessary co-factor or nutrient to increase the activity of the enzyme. In one embodiment, the compound or element which increases glutathione activity peroxidase is methionine, selenium or a selenium containing compound. In one embodiment, selenium promotes synthesis of selenoproteins including mammalian glutathione peroxidases 1, 2, 3, 4, and 6. Glutathione peroxidases are present in follicular melanocytes and are hydrogen peroxide reducing enzymes. Moreover, selenium promotes the synthesis of selenocysteine which is a cofactor for glutathione peroxidase activity. As a result, selenium promotes the activity of glutathione peroxidase in at least two ways, thereby reducing hydrogen peroxide levels in follicular melanocytes.

In another embodiment, the selenium-containing compound is provided in the form of selenium amino acid complex, L-selenomethionine, L-selenocysteine, selenium yeast, selenium proteinate, selenium chelate, sodium selenite or sodium selenate.

In another embodiment, the formulation further comprises one or more vitamins. In another embodiment, the formulation further comprises vitamin B6, vitamin B12, and folic acid, alone or in any combination. In one embodiment, vitamin B6 and folic acid aid in the chelation of L-methionine with hydrogen peroxide, and therefore, can be provided to supplement the levels of these vitamins. In a further embodiment, vitamin B12 is utilized in the production of melanin in the body, and therefore, can be provided to supplement such levels to ensure production of melanin.

In one embodiment, the formulation further comprises a free radical scavenger, optionally a scavenger which doesn't produce hydrogen peroxide. In one embodiment, the free radical scavenger is pterostilbene.

In another embodiment, the formulation further comprises a biomolecule absorption enhancing agent which increases gastrointestinal absorption and systemic availability (i.e. increased blood/plasma levels) of at least one co-administered biomolecule, nutrient or other compound for which it is desired to increase the absorption. A large number of biomolecule absorption enhancing agents are known in the art including, as non-limiting examples, surfactants, bile salts, $Ca^{2+}$ chelating agents, fatty acids, medium chain glycerides, acyl carnitine, alkanoyl cholines, N-acetylated α-amino acids, N-acetylated non-α-amino acids, chitosans, mucoadhesive polymers, phospholipids (see for example, J Pharm Sci., 2000 April; 89(4):429-42; Adv Drug Deliv Rev. 1997; 23:163-83). Other examples of biomolecule absorption enhancing agent include natural plant extracts, such as, *Astragalus membranaceus* and *Panax notoginseng* extracts. In another embodiment, the biomolecule absorption enhancing agent is AstraGin™ (AstraGin™ is a biomolecule absorption enhancing agent consisting of extracts of *Astragalus membranaceus* and *Panax notoginseng* marketed by NuLiv Science USA, Inc.). In one embodiment, the biomolecule absorption enhancing agent, such as Astragin, increases the abosprtion of amino acids by at least 50%, or by about 60%, and/or increases the absorption of vitamins by about 40%, or by about 50%. The term biomolecule as used herein includes enzymes, proteins, amino acids, nutrients and/or vitamins.

In another embodiment of the disclosure, the oral pharmaceutical formulation comprises:
a) at least one hydrogen peroxide reducing enzyme present in an amount from 0.0001 IU to more than 10,000 IU;
b) at least one hydrogen peroxide scavenger present in an amount between 0.0001 μg to 3 g, optionally between 1 mg and 500 mg, optionally between 50 mg and 250 mg, or about 100 mg; and
c) at least one compound or element which increases glutathione peroxidase activity in vivo present in an amount between 0.0001 μg to 3 g, optionally between 1 μg and 400 μg, optionally 150 μg and 200 μg, or about 180 μg.

In another embodiment of the disclosure, the oral pharmaceutical formulation comprises:
a) at least one hydrogen peroxide reducing enzyme present in an amount greater than 5,000 IU;
b) at least one hydrogen peroxide scavenger present in an amount between 0.0001 μg to 3 g, optionally between 1 mg and 500 mg, optionally between 50 mg and 250 mg, or about 100 mg; and
c) at least one compound or element which increases glutathione peroxidase activity in vivo present in an amount between 0.0001 μg to 3 g, optionally between 1 μg and 400 μg, optionally 150 μg and 200 μg, or about 180 μg.

In another embodiment of the disclosure, the oral pharmaceutical formulation comprises:
a) at least one hydrogen peroxide reducing enzyme present in an amount greater than 5,000 IU;
b) at least one hydrogen peroxide scavenger present in an amount between 0.0001 μg to 3 g, optionally between 1 mg and 500 mg, optionally between 50 mg and 250 mg, or about 100 mg;
c) at least one compound or element which increases glutathione peroxidase activity in vivo present in an amount between 0.0001 μg to 3 g, optionally between 1 μg and 400 μg, optionally 150 μg and 200 μg, or about 180 μg;
d) a biomolecule absorption enhancing agent, such as Astragin, in an amount between 0.0001 μg to 3 g, optionally between 1 mg and 50 mg, optionally between 1 mg and 10 mg, or about 6 mg.

In a particular embodiment, the formulation consists of:
a) Catalase present in an amount of 10,000 IU or greater,
b) L-methionine present in an amount between 0.0001 μg to 3 g, optionally between 1 mg and 500 mg, optionally between 50 mg and 250 mg, or about 100 mg,
c) selenium amino acid complex present in an amount between 0.0001 μg to 3 g, optionally between 1 μg and 400 μg, optionally 150 μg and 200 μg, or about 180 μg,
d) pterostilbene present in an amount between 0.0001 μg to 3 g, optionally between 1 mg and 100 μg, optionally between 1 μg and 50 μg, or about 20 μg;
e) vitamin B6 present in an amount between 0.0001 μg to 3 g, optionally between about 1 μg and 100 μg, optionally between 1 μg and 10 μg, or about 4 μg;
f) vitamin B12 present in an amount between 0.0001 μg to 3 g, optionally between about 1 μg and 100 μg, optionally between about 1 μg and 20 μg, or about 12 μg;
g) folic acid present in an amount between 0.0001 μg to 3 g, optionally between about 1 μg and 1000 μg, optionally between about 100 μg and 800 μg, or about 200 μg; and
h) AstraGin™ present in an amount between 0.0001 μg to 3 g, optionally between 1 mg and 50 mg, optionally between 1 mg and 10 mg, or about 6 mg.

In one embodiment the formulation is formulated as an enteric coated liquid capsule. The enteric coating of the liquid capsules prevents damage to active ingredients of the formulation during passage through the stomach and promotes delivery of the formulation to the small intestine. It will be understood that there are difficulties with using liquid capsules with such formulations because the liquid pH must be neutral to slightly basic, and therefore, oils cannot be used in the capsules. In one embodiment, the oral formulation is in the form of an aqueous mixture.

In another embodiment, the formulation is used for the treatment or prevention of canities. In another embodiment, the treatment results in at least 5 percent restoration of pre-canities hair pigmentation. In another embodiment, the treatment results in at least 25 percent restoration of pre-canities hair pigmentation. In another embodiment, the treatment results in at least 50 percent restoration of pre-canities hair pigmentation. In another embodiment, the treatment results in at least 100 percent restoration of pre-canities hair pigmentation. In one embodiment, formulations as taught in the Examples were found to increase the amount of pigmented hair, or lessen the amount of grey hair, by at least 5%.

(II) Methods

In one embodiment is provided a method of producing the formulation in enteric coated liquid capsules without leakage. The capsules, banded or un-banded, are first filled with the formulation using methods commonly known to those skilled in the art.

In one embodiment, a two-piece capsule is filled with the formulation and the two pieces are wrapped (banded) with an adhesive to join the capsule together to prevent it from leaking or splitting apart.

The liquid-filled capsules are treated with a sealant before treatment with an acid resistant coating. The liquid sealant is a coating which acts as a barrier to control the location in the digestive system where the formulation is absorbed. In one embodiment, the liquid sealant is applied as an aqueous mixture of, for example, Nutrateric® (Colorcon).

The capsules are then coated with an acid resistant coating which slows, resists or stops the degradation of the capsule from undergoing acid erosion in an acidic environment. This method prevents leakage during the enteric coating process.

In another embodiment is provided a method of treating human canities using the disclosed oral formulations. Use of oral pharmaceutical formulations in the treatment of canities offers advantages over topical treatments including the ease of administration and systemic dispersal which alleviates concerns of uneven application.

Certain embodiments of the invention are disclosed below by way of example.

EXAMPLES

Example 1

Preparation of Powdered Oral Formulation

L-Methionine (100 mg), Catalase (10,000 IU), Vitamin B6 (4 mg), Folic Acid (200 µg), Vitamin B12 (12 µg), and selenium (180 µg) powders were combined in a non-shear blender and mixed until a uniform powdered mixture was obtained. Microcrystalline cellulose and magnesium stearate were subsequently added.

Example 2

Preparation of Liquid Capsule Oral Formulation

L-Methionine (100 mg) was mixed in a shear mixer with purified water to both reduce particle size and liquefy the ingredients. All the other ingredients (Catalase (10,000 IU), Vitamin B6 (4 mg), Folic Acid (200 µg), Vitamin B12 (12 µg), Selenium (180 µg), Pterostilbene (20 mg), AstraGin (6 mg)) were then combined with the L-methionine in a non-shear blender and mixed until a uniform aqueous mixture was obtained. 10% by volume glycerin was then added as a sterilizing agent to prevent the growth of microbes improving shelf stability. Silica was then added as a viscosity modifier so that the water and glycerin remains bonded with the other ingredients preventing capsule dissolution from within.

Example 3

Preparation of Enteric Coated Liquid Capsule

The liquid capsule oral formulation of Example 2 is enterically coated with Nutrateric® (Colorcon) in an amount between 3-7% by weight of the capsule in a process temperature not exceeding 35° C., resulting enteric coated capsules having approximately 2 hours of acid protection time in the stomach, and a dissolution time of approximately 45 minutes in the small intestine.

Example 4

In Vivo Administration of Formulation Containing Catalase at 5,000 IU

An oral formulation containing 5,000 IU of catalase was administered to a subject. The formulation did not improve the grey hair of the subject.

Example 5

In Vivo Administration of Enteric Coated Capsule Formulation Containing Catalase at 10,000 IU An enteric coated capsule oral formulation was administered to a subject which contained 10,000 IU, methionine and selenium. Upon quantitative visual inspection, the formulation was found to reverse the amount of grey hair, compared to the hair before taking the formulation.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

I claim:

1. A method of treating or preventing canities comprising administering to a subject an oral pharmaceutical formulation, the formulation comprising:
   a) a therapeutically effective amount of at least one hydrogen peroxide reducing enzyme, wherein the therapeutically effective amount of the hydrogen peroxide reducing enzyme comprises an amount of 15,000 U or greater.

2. The method of claim 1, wherein the formulation further comprises therapeutically effective amounts of:
   a) at least one hydrogen peroxide scavenger; and
   b) at least one compound or element which increases glutathione peroxidase activity in vivo.

3. The method of claim 1, wherein the hydrogen peroxide reducing enzyme is a peroxidase.

4. The method of claim 3, wherein the peroxidase is a catalase or a glutathione peroxidase.

5. The method of claim 2, wherein the hydrogen peroxide scavenger is an amino acid.

6. The method of claim 5, wherein the amino acid is methionine, cysteine, selenocysteine or tyrosine.

7. The method of claim 6, wherein the amino acid is methionine.

8. The method of claim 2, wherein the compound or element which increases glutathione activity peroxidase is methionine, selenium or a selenium containing compound.

9. The method of claim 8, wherein the selenium containing compound is selenium amino acid complex, L-selenomethionine, L-selenocysteine, selenium yeast, selenium proteinate, selenium chelate, sodium selenite or sodium selenate.

10. The method of claim 1, wherein the formulation further comprises pterostilbene.

11. The method of claim 1, wherein the formulation further comprises a biomolecule absorption enhancing agent.

12. The method of claim 2, wherein the formulation comprises:
   a) at least one hydrogen peroxide reducing enzyme present in an amount of 15,000 U or greater;
   b) at least one hydrogen peroxide scavenger present in an amount between 0.0001 µg to 3 g; and
   c) at least one compound or element which increases glutathione peroxidase activity in vivo present in an amount between 0.0001 µg to 3 g.

13. The method of claim 12, wherein the formulation comprises:
   a) at least one hydrogen peroxide reducing enzyme present in an amount of 15,000 U or greater;
   b) at least one hydrogen peroxide scavenger present in an amount between 1 mg and 500 mg; and
   c) at least one compound or element which increases glutathione peroxidase activity in vivo present in an amount 1 µg and 400 µg.

14. The method of claim 1, wherein the formulation consists of:
   a) Catalase present in an amount of 15,000 U or greater,
   b) L-methionine present in an amount between 0.0001 µg to 3 g,
   c) selenium amino acid complex present in an amount between 0.0001 µg to 3 g,
   d) pterostilbene present in an amount between 0.0001 µg to 3 g,
   e) vitamin B6 present in an amount between 0.0001 µg to 3 g,
   f) vitamin B12 present in an amount between 0.0001 µg to 3 g,
   g) folic acid present in an amount between 0.0001 µg to 3 g, and
   h) a biomolecule absorption enhancing agent present in an amount between 0.0001 µg to 3 g.

15. The method of claim 1, wherein the treatment results in at least 5 percent restoration of pre-canities hair pigmentation.

16. The method of claim 1, wherein the oral pharmaceutical formulation is in the form of an enteric coated liquid capsule.

17. The method of claim 16, wherein the formulation further comprises therapeutically effective amounts of:
   a) at least one hydrogen peroxide scavenger;
   b) at least one compound or element which increases glutathione peroxidase activity in vivo; and
   c) a biomolecule absorption enhancing agent.

* * * * *